United States Patent [19]
Debonte et al.

[11] Patent Number: 5,861,187
[45] Date of Patent: *Jan. 19, 1999

[54] OIL FROM CANOLA SEED WITH ALTERED FATTY ACID PROFILES AND A METHOD OF PRODUCING OIL

[75] Inventors: Lorin Roger Debonte; Zhegong Fan, both of Delran, N.J.; Willie Hsiao-Tsu Loh, Philadelphia, Pa.

[73] Assignee: Cargill, Incorporated, Wayzata, Minn.

[*] Notice: The term of this patent shall not extend beyond the expiration date of Pat. No. 5,668,299.

[21] Appl. No.: 415,553

[22] Filed: Apr. 3, 1995

Related U.S. Application Data

[60] Division of Ser. No. 170,886, Dec. 21, 1993, abandoned, which is a continuation-in-part of Ser. No. 739,965, Aug. 5, 1991, abandoned, which is a continuation-in-part of Ser. No. 575,542, Aug. 30, 1990, abandoned.

[51] Int. Cl.$^6$ .............................. A23D 9/00; A01H 1/06; A01H 5/10; E12N 15/00
[52] U.S. Cl. .......................... 426/601; 426/417; 426/489; 800/230; 800/200; 800/255; 800/205; 800/DIG. 17; 800/DIG. 9; 47/58.03; 47/58.05; 435/172.1
[58] Field of Search ..................................... 426/601, 417, 426/489; 800/230, 200, 255, 205, DIG. 17, DIG. 9; 47/58.03, 58.05; 435/172.1

[56] References Cited

U.S. PATENT DOCUMENTS 4,627,192 12/1986 Fick .
4,948,811 8/1990 Spinner et al. .

FOREIGN PATENT DOCUMENTS 323 753 7/1989 European Pat. Off. .
WO 91/15578 10/1991 WIPO .

OTHER PUBLICATIONS

Swern 1979 Bailey's Industrial Oil and Fat Products vol. 1 4th ed. John Wiley & Sons New York pp. 413–421 Sebedio 1981 JAOCS 58(11) 972–3.
Downey et al., "Genetic Control of Fatty Acid Composition in Oilseed Crops", Proc. Flax Inst. USA, vol. 47, No. 3, pp. 1–3 (1971).
J.K. Daun, "The Introduction of Low Erucic Acid Rapeseed Varieties into Canadian Production", High and Low Erucic Acid Rapeseed Oils—Production, Usage, Chemistry, and Toxicological Evaluation, pp. 162–180 (1983).
V.I. Shpota, "Rape and Mustard Breeding for Oil Quality", Proceedings of the International Rapeseed Conference, Poznan, Poland, pp. 560–565 (May 1987).
Shpota et al., The Basis Material for Selection of Winter Rapeseed for Quality of Oil and Oil Cakes; Bulletin of Science and Technology Information, the All–Union Oil Bearing Crops Research Institute, 1981, Issue #78.
Conner et al., Coronary Heart Disease: Prevention, Complications, and Treatment, 43–46, 1985.
F.H. Mattson, J. Am. Diet. Assoc., 89, 387–390, 1989.
Mensink et al., New England J. Med., 321, 436–441, 1989.
S.M. Grundy, New England J. Med., 314, 745–748, 1986.
Garg et al., New England J. Med., 319, 829–834, 1988.
Williams et al., J. Am. Med. Assoc., 257, 3251–3256, 1987.
A. Keys, Circulation, 44(Suppl), 1, 1970.
Pleines and Friedt, Fat Sci. Technol., 90(5), 167–171, 1988.
Rakow and McGregor, J. Amer. Oil Chem. Soc., 50, 400–403, Oct. 1973.
Roy and Tarr, Pflansenzuchtg, 95(3), 201–209, 1985.
Roy and Tarr, Plant Breeding, 98, 89–96, 1987.
Canvin, Can. J. Botany, 43, 63–69, 1965.
G.Z. Gaul, Radiation Botany, 4, 155–232, 1964.
G.Z. Rakow, Pflanzenzuchtg, 69, 62–82, 1973.
Scarth et al., Can. J. Plant Sci., 68, 509–511, 1988.
Downey et al., Can. J. Plant Sci., 43, 271, 1963.
B.R. Stefanson, In; High and Low Erucic Acid Rapeseed Oils, Ed. N.T. Kenthies, Academic Press Inc., Canada, 145–159, 1983.
G. Robbelen, In; Biotechnology for the Oils and Fats Industry, American Oil Chemists Society, 97–105, 1984.
Kardia et al., Can. J. Plant Sci., 56, 561–966, 1976.
Kirk–Othmer Encyclopedia of Chemical Technol., 3rd Edition, 9, 795–831, 1980.
Pleins et al., Abstract of Proceedings of the 7th International Rapeseed Congress, Pozman, Poland, May 11–14, 1987.
Tremolieres et al., Phytochemistry, 21(1), 41–45, 1982.
Robbelen et al., Pflanzenauchtg, 75, 93–105, 1985.
Robbelen et al., Proceedings of the International Conference on the Scientific, Technology, and Marketing of Rapeseed and Rapeseed Products, Sep. 20–23, 1970.
Pleins et al., Abstract of 43rd Lecture Meeting of Deutsche Gesellschaft fur Feltwissenschaft in Hamburg, Sep. 30–Oct. 11, 1987.
Brunklaus–Jung et al., Plant Breeding, 98, 9–16, 1987.
Hoffman et al., Theor. Appl. Genet., 61 225–232 1982.
Kondra et al., Selection for Oleic, Linoleic and Linolenic Acid Content in $F_2$ Populations of Rape, Can. J. Plant Sci., 56, 961–966, 1976.
Jonsson et al., "Quality Breeding in Rapeseed", Research and Results in Plant Breeding, Svalof 1886–1986, pp. 173–184.

Primary Examiner—Carolyn Paden
Attorney, Agent, or Firm—Fish & Richardson P.C., P.A.

[57] ABSTRACT

The oil from a canola seed with an altered fatty acid profile is disclosed to have low FDA saturates; high oleic acid; low linoleic acid; low stearic acid; and low linoleic acid plus linolenic acid. The method for extracting the oil from the seeds is also disclosed.

17 Claims, No Drawings

OIL FROM CANOLA SEED WITH ALTERED FATTY ACID PROFILES AND A METHOD OF PRODUCING OIL

CROSS REFERENCE TO RELATED APPLICATION

This application is a divisional of copending application Ser. No. 08/170,886, filed Dec. 21, 1993, now abandoned which is a continuation-in-part of U.S. Ser. No. 07/739,965, filed Aug. 5, 1991, which is a continuation-in-part of U.S. Ser. No. 07/575,542, filed Aug. 30, 1990.

TECHNICAL FIELD

This invention relates to improved Brassica seeds, plants and oils having altered fatty acid profiles which provide advantageous nutritional or manufacturing properties.

BACKGROUND OF THE INVENTION

Diets high in saturated fats increase low density lipoproteins (LDL) which mediate the deposition of cholesterol on blood vessels. High plasma levels of serum cholesterol are closely correlated with atherosclerosis and coronary heart disease (Conner et al., Coronary Heart Disease: Prevention, Complications, and Treatment, pp. 43–64, 1985). By producing oilseed Brassica varieties with reduced levels of individual and total saturated fats in the seed oil, oil-based food products which contain less saturated fats can be produced. Such products will benefit public health by reducing the incidence of atherosclerosis and coronary heart disease.

The dietary effects of monounsaturated fats have also been shown to have dramatic effects on health. Oleic acid, the only monounsaturated fat in most edible vegetable oils, lowers LDL as effectively as linoleic acid, but does not affect high density lipoproteins (HDL) levels (Mattson, F. H., J. Am. Diet. Assoc., 89:387–391, 1989; Mensink et al., New England J. Med., 321:436–441, 1989). Oleic acid is at least as effective in lowering plasma cholesterol as a diet low in fat an high in carbohydrates (Grundy, S. M., New England J. Med., 314:745–748, 1986; Mensink et al., New England J. Med., 321:436–441, 1989). In fact, a high oleic acid diet is preferable to low fat, high carbohydrate diets for diabetics (Garg et al., New England J. Med., 319:829–834, 1988). Diets high in monounsaturated fats are also correlated with reduced systolic blood pressure (Williams et al., J. Am. Med. Assoc., 257:3251–3256, 1987). Epidemiological studies have demonstrated that the "Mediterranean" diet, which is high in fat and monounsaturates, is not associated with coronary heart disease (Keys, A., Circulation, 44(Suppl): 1, 1970).

Many breeding studies have been conducted to improve the fatty acid profile of Brassica varieties. Pleines and Friedt, Fat Sci. Technol., 90(5), 167–171 (1988) describe plant lines with reduced $C_{18:3}$ levels (2.5–5.8%) combined with high oleic content (73–79%). Rakow and McGregor, J. Amer. Oil Chem. Soc., 50,400–403 (Oct. 1973) discuss problems associated with selecting mutants for linoleic and linolenic acids. In Can. J. Plant Sci, 68, 509–511 (Apr. 1988) Stellar summer rape producing seed oil with 3% linolenic acid and 28% linoleic acid is disclosed. Roy and Tarr, Z. Pflanzenzuchtg, 95(3), 201–209 (1985) teaches transfer of genes through an interspecific cross from *Brassica juncea* into *Brassica napus* resulting in a reconstituted line combining high linoleic with low linolenic acid content. Roy and Tarr, Plant Breeding, 98, 89–96 (1987) discuss prospects for development of *B. napus* L. having improved linolenic and linolenic acid content. European Patent application 323,751 published Jul. 12, 1989 discloses seeds and oils having greater than 79% oleic acid combined with less than 3.5% linolenic acid. Canvin, Can. J. Botany, 43, 63–69 (1965) discusses the effect of temperature on the fatty acid composition of oils from several seed crops including rapeseed.

Mutations are typically induced with extremely high doses of radiation and/or chemical mutagens (Gaul, H. Radiation Botany (1964) 4:155–232). High dose levels which exceed LD50, and typically reach LD90, led to maximum achievable mutation rates. In mutation breeding of Brassica varieties high levels of chemical mutagens alone or combined with radiation have induced a limited number of fatty acid mutations (Rakow, G. Z. Pflanzenzuchtg (1973) 69:62–82). The low α-linolenic acid mutation derived from the Rakow mutation breeding program did not have direct commercial application because of low seed yield. The first commercial cultivar using the low α-linolenic acid mutation derived in 1973 was released in 1988 as the variety Stellar (Scarth, R. et al., Can. J. Plant Sci. (1988) 68:509–511). Stellar was 20% lower yielding than commercial cultivars at the time of its release.

Canola-quality oilseed Brassica varieties with reduced levels of saturated fatty acids in the seed oil could be used to produce food products which promote cardiovascular health. Canola lines which are individually low in palmitic and stearic acid content or low in combination will reduce the levels of saturated fatty acids. Similarly, Brassica varieties with increased monounsaturate levels in the seed oil, and products derived from such oil, would improve lipid nutrition. Canola lines which are low in linoleic acid tend to have high oleic acid content, and can be used in the development of varieties having even higher oleic acid content.

Increased palmitic acid content provides a functional improvement in food applications. Oils high in palmitic acid content are particularly useful in the formulation of margarines. Thus, there is a need for manufacturing purposes for oils high in palmitic acid content.

Decreased alpha linolenic acid content provides a functional improvement in food applications. Oils which are low in linolenic acid have increased stability. The rate of oxidation of lipid fatty acids increases with higher levels of linolenic acid leading to off-flavors and off-odors in foods. There is a need in the food industry for oils low in alpha linolenic acid.

SUMMARY OF THE INVENTION

The present invention comprises canola seeds, plant lines producing seeds, and plants producing seed, said seeds having a maximum content of FDA saturates of about 5% and a maximum erucic acid content of about 2% based upon total extractable oil and belonging to a line in which said saturates content has been stabilized for both the generation to which the seed belongs and its parent generation. Progeny of said seeds and canola oil having a maximum erucic acid content of about 2%, based upon total extractable oil, are additional aspects of this invention. Preferred are seeds, plant lines producing seeds, and plants producing seeds, said seeds having an FDA saturates content of from about 4.2% to about 5.0% based upon total extractable oil.

The present invention further comprises Brassica seeds, plant lines producing seeds, and plants producing seeds, said seeds having a minimum oleic acid content of about 71% based upon total extractable oil and belonging to a line in which said oleic acid content has been stabilized for both the generation to which the seed belongs and its parent generation. A further aspect of this invention is such high oleic acid seeds additionally having a maximum erucic acid content of about 2% based upon total extractable oil. Progeny of said seeds; and Brassica oil having 1) a minimum oleic acid content of about 71% or 2) a minimum oleic acid content of about 71% and a maximum erucic content of about 2% are also included in this invention. Preferred are seeds, plant lines producing seeds, and plants producing seeds, said seeds having an oleic acid content of from about 71.2% to about 78.3% based upon total extractable oil.

The present invention further comprises canola seeds, plant lines producing seeds, and plants producing seeds, said seeds having a maximum linoleic acid content of about 14% and a maximum erucic acid content of about 2% based upon total extractable oil and belonging to a line in which said acid content is stabilized for both the generation to which the seed belongs and its parent generation. Progeny of said seeds and canola oil having a maximum linoleic acid content of about 14% and a maximum erucic acid content of about 2%, are additional aspects of this invention. Preferred are seeds, plant lines producing seeds, and plants producing seeds, said seeds having a linoleic acid content of from about 8.4% to about 9.4% based upon total extractable oil.

The present invention further comprises Brassica seeds, plant lines producing seeds, and plants producing seeds, said seeds having a maximum palmitic acid content of about 3.5% and a maximum erucic acid content of about 2% based on total extractable oil and belonging to a line in which said acid content is stabilized for both the generation to which the seed belongs and its parent generation. Progeny of said seeds and canola having a maximum palmitic acid content of about 3.5% and a maximum erucic acid content of about 2%, are additional aspects of this invention. Preferred are seeds, plant lines producing seeds, and plants producing seeds, said seeds having a palmitic acid content of from about 2.7% to about 3.1% based upon total extractable oil.

The present invention further comprises Brassica seeds, plant lines producing seeds, and plants producing seeds, said seeds having a minimum palmitic acid content of about 9.0% based upon total extractable oil and belonging to a line in which said acid content is stabilized for both the generation to which the seed belongs and its parent generation. A further aspect of this invention is such high palmitic acid seeds additionally having a maximum erucic acid content of about 2% based upon total extractable oil. Progeny of said seeds; and Brassica oil having 1) a minimum palmitic acid content of about 9.0%, or 2) a minimum palmitic acid content of about 9.0% and a maximum erucic acid content of about 2% are also included in this invention. Preferred are seeds, plant lines producing seeds, and plants producing seeds, said seeds having a palmitic acid content of from about 9.1% to about 11.7% based upon total extractable oil.

The present invention further comprises Brassica seeds, plant lines producing seeds, and plants producing seeds, said seeds having a maximum stearic acid content of about 1.1% based upon total extractable oil and belonging to a line in which said acid content is stabilized for both the generation to which the seed belongs and its parent generation. Progeny of said seeds have a canola oil having a maximum stearic acid content of about 1.1% and maximum erucic acid content of about 2%. Preferred are seeds, plant lines producing seeds, and plants producing seeds having a palmitic acid content of from about 0.8% to about 1.1% based on total extractable oil.

The present invention further comprises Brassica seeds, plant lines producing seeds, and plants producing seeds, said seeds having a sum of linoleic acid content and linolenic acid content of a maximum of about 14% based upon total extractable oil and belonging to a line in which said acid content is stabilized for both the generation to which the seed belongs and its parent generation. Progeny of said seeds have a canola oil having a sum of linoleic acid content and linolenic acid content of a maximum of about 14% and a maximum erucic acid content of about 2%. Preferred are seeds, plant lines producing seeds, and plants producing seeds having a sum of linoleic acid content and linolenic acid content of from about 11.8% to about 12.5% based on total extractable oil.

DETAILED DESCRIPTION OF THE INVENTION

The U.S. Food and Drug Administration defines saturated fatty acids as the sum of lauric ($C_{12:0}$), myristic ($C_{14:0}$), palmitic ($C_{16:0}$) and stearic ($C_{18:0}$) acids. The term "FDA saturates" as used herein means this above-defined sum. Unless total saturate content is specified, the saturated fatty acid values expressed here include only "FDA saturates".

All percent fatty acids herein are percent by weight of the oil of which the fatty acid is a component.

As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production.

As used herein, "mutation" refers to a detectable and heritable genetic change not caused by segregation or genetic recombination. "Mutant" refers to an individual, or lineage of individuals, possessing a genetic mutation. The term "Mutagenesis" refers to the use of a mutagenic agent to induce random genetic mutations within a population of individuals. The treated population, or a subsequent generation of that population, is then screened for usable trait(s) that result from the mutations. A "population" is any group of individuals that share a common gene pool. As used herein "$M_0$" is untreated seed. As used herein, "$M_1$" is the seed (and resulting plants) exposed to a mutagenic agent, while "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation.

The term "progeny" as used herein means the plants and seeds of all subsequent generations resulting from a particular designated generation.

The term "selfed" as used herein means self-pollinated.

"Stability" or "stable" as used herein means that with respect to a given fatty acid component, the component is maintained from generation to generation for at least two generations and preferably at least three generations at substantially the same level, e.g., preferably ±5%. The method of invention is capable of creating lines with improved fatty acid compositions stable up to ±5% from generation to generation. The above stability may be affected by temperature, location, stress and time of planting. Thus, comparison of fatty acid profiles should be made from seeds produced under similar growing conditions. Stability may be measured based on knowledge of prior generation.

Intensive breeding has produced Brassica plants whose seed oil contains less than 2% erucic acid. The same varieties have also been bred so that the defatted meal contains less than 30 μmol glucosinolates/gram. "Canola" as used herein refers to plant variety seed or oil which contains less than 2% erucic acid ($C_{22:1}$), and meal with less than 30 μmol glucosinolates/gram.

Seeds of Westar, a Canadian (*Brassica napus*) spring canola variety, were subject to chemical mutagenesis. Mutagenized seeds were planted in the greenhouse and the plants were self-pollinated. The progeny plants were individually analyzed for fatty acid composition, and regrown either in the greenhouse or in the field. After four successive generations of self-pollinations, followed by chemical analysis of the seed oil at each cycle, several lines were shown to carry stably inherited mutations in specific fatty acid components, including reduced palmitic acid ($C_{16:0}$), increased palmitic acid, reduced stearic acid ($C_{18:0}$), increased oleic acid ($C_{18:1}$), reduced linoleic acid ($C_{18:2}$) and reduced linolenic acid ($C_{18:3}$), in the seed oil.

The general experimental scheme for developing lines with stable fatty acid mutations is shown in Scheme I hereinafter.

SCHEME I

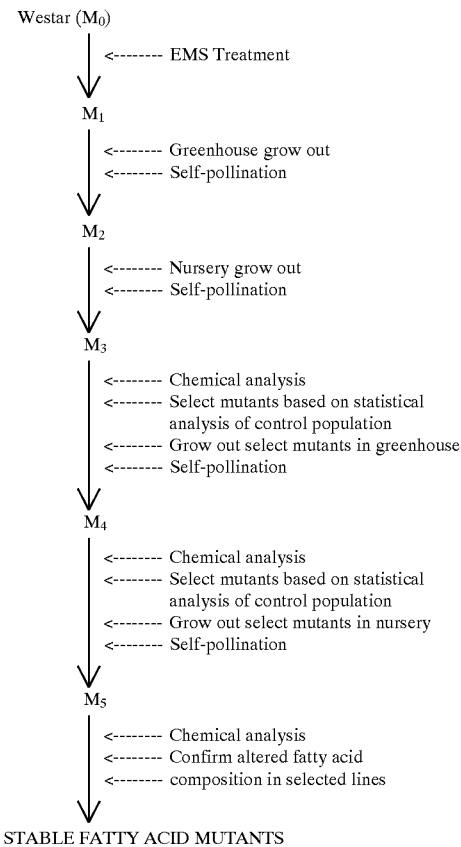

STABLE FATTY ACID MUTANTS

Westar seeds ($M_0$) were mutagenized with ethylmethane-sulfonate (EMS). Westar is a registered Canadian spring variety with canola quality. The fatty acid composition of field-grown Westar, 3.9% $C_{16:0}$, 1.9% $C_{18:0}$, 67.5% $C_{18:1}$, 17.6% $C_{18:2}$, 7.4% $C_{18:3}$, <2% $C20:1+C_{22:1}$, has remained stable under commercial production, with <±10% deviation, since 1982. The disclosed method may be applied to all oilseed Brassica species, and to both Spring and Winter maturing types within each species. Physical mutagens, including but not limited to X-rays, UV rays, and other physical treatments which cause chromosome damage, and other chemical mutagens, including but not limited to ethidium bromide, nitrosoguanidine, diepoxybutane etc. may also be used to induce mutations. The mutagenesis treatment may also be applied to other stages of plant development, including but not limited to cell cultures, embryos, microspores and shoot apices. The $M_1$ seeds were planted in the greenhouse and $M_1$ plants were individually self-pollinated.

$M_2$ seed was harvested from the greenhouse and planted in the field in a plant-to-row design. Each plot contained six rows, and five $M_2$ lines were planted in each plot. Every other plot contained a row of non-mutagenized Westar as a control. Based on gas chromatographic analysis of $M_2$ seed, those lines which had altered fatty acid composition were self-pollinated and individually harvested.

$M_3$ seeds were evaluated for mutations on the basis of a Z-distribution. An extremely stringent 1 in 10,000 rejection rate was employed to establish statistical thresholds to distinguish mutation events from existing variation. Mean and standard deviation values were determined from the non-mutagenized Westar control population in the field. The upper and lower statistical thresholds for each fatty acid were determined from the mean value of the population±the standard deviation, multiplied by the Z-distribution. Based on a population size of 10,000, the confidence interval is 99.99%.

Seeds ($M_3$) from those $M_2$ lines which exceeded either the upper or lower statistical thresholds were replanted in the greenhouse and self-pollinated. This planting also included Westar controls. The $M_4$ seed was re-analyzed using new statistical thresholds established with a new control population. Those $M_4$ lines which exceeded the new statistical thresholds for selected fatty acid compositions were advanced to the nursery. Following self-pollination, $M_5$ seed from the field were re-analyzed once again for fatty acid composition. Those lines which remained stable for the selected fatty acids were considered stable mutations. "Stable mutations" as used herein are defined as $M_5$ or more advanced lines which maintain a selected altered fatty acid profile for a minimum of three generations, including a minimum of two generations under field conditions, and exceeding established statistical thresholds for a minimum of two generations, as determined by gas chromatographic analysis of a minimum of 10 randomly selected seeds bulked together. Alternatively, stability may be measured in the same way by comparing to subsequent generations. In subsequent generations, stability is defined as having similar fatty acid profiles in the seed as that of the prior or subsequent generation when grown under substantially similar conditions.

The amount of variability for fatty acid content in a seed population is quite significant when single seeds are analyzed. Randomly selected single seeds and a ten seed bulk sample of a commercial variety were compared. Significant variation among the single seeds was detected (Table A). The half-seed technique (Downey, R. K. and B. L. Harvey, Can. J. Plant Sci., 43:271 [1963]) in which one cotyledon of the germinating seed is analyzed for fatty acid composition and the remaining embroyo grown into a plant has been very useful to plant breeding work to select individuals in a population for further generation analysis. The large variation seen in the single seed analysis (Table A) is reflected in the half-seed technique.

TABLE A

Single Seed Analysis for Fatty Acid Composition[1]

| SAMPLE | 16:0 | 16:1 | 18:0 | 18:1 | 18:2 | 18:3 | 20:0 | 20:1 | 22:0 | 22:1 |
|---|---|---|---|---|---|---|---|---|---|---|
| Bulk | 3.2 | 0.4 | 1.8 | 20.7 | 13.7 | 9.8 | 0.8 | 11.2 | 0.4 | 32.2 |
| 1 | 2.8 | 0.2 | 1.1 | 14.6 | 14.6 | 11.1 | 0.8 | 9.8 | 0.7 | 38.2 |
| 2 | 3.3 | 0.2 | 1.3 | 13.1 | 14.4 | 11.7 | 0.9 | 10.5 | 0.7 | 37.0 |
| 3 | 3.0 | — | 1.2 | 12.7 | 15.3 | 10.6 | 0.8 | 7.3 | 0.7 | 43.2 |
| 4 | 2.8 | 0.2 | 1.1 | 16.7 | 13.2 | 9.1 | 0.8 | 11.2 | 0.4 | 38.9 |
| 5 | 3.0 | — | 1.8 | 15.2 | 13.3 | 8.4 | 1.3 | 8.7 | 0.9 | 42.3 |
| 6 | 3.1 | — | 1.3 | 14.4 | 14.6 | 10.3 | 1.0 | 10.9 | 0.8 | 39.3 |
| 7 | 2.6 | — | 1.2 | 15.7 | 13.8 | 9.9 | 0.9 | 12.2 | 0.5 | 37.0 |
| 8 | 3.1 | — | 1.1 | 16.2 | 13.4 | 10.6 | 0.6 | 9.2 | 0.8 | 41.4 |
| 9 | 2.7 | 0.1 | 1.0 | 13.5 | 11.2 | 11.3 | 0.8 | 6.2 | 0.7 | 46.9 |
| 10 | 3.4 | 0.2 | 1.4 | 13.9 | 17.5 | 10.8 | 1.1 | 10.0 | 0.9 | 36.2 |
| 11 | 2.8 | 0.2 | 1.2 | 12.7 | 12.9 | 10.3 | 1.0 | 7.9 | 0.9 | 43.3 |
| 12 | 2.3 | 0.1 | 1.6 | 20.7 | 14.8 | 6.5 | 1.1 | 12.5 | 0.8 | 34.5 |
| 13 | 2.6 | 0.2 | 1.3 | 21.0 | 11.4 | 7.6 | 1.0 | 11.6 | 0.6 | 36.7 |
| 14 | 2.6 | 0.1 | 1.2 | 14.7 | 13.2 | 9.4 | 0.9 | 10.1 | 0.8 | 40.8 |
| 15 | 2.9 | 0.2 | 1.4 | 16.6 | 15.1 | 11.2 | 0.7 | 9.1 | 0.3 | 36.1 |
| 16 | 3.0 | 0.2 | 1.1 | 12.4 | 13.7 | 10.4 | 0.9 | 8.7 | 0.8 | 42.7 |
| 17 | 2.9 | 0.1 | 1.1 | 21.1 | 12.3 | 7.1 | 0.8 | 12.4 | 0.5 | 36.8 |
| 18 | 3.1 | 0.1 | 1.2 | 13.7 | 13.1 | 10.4 | 1.0 | 8.8 | 0.7 | 41.6 |
| 19 | 2.7 | 0.1 | 1.0 | 11.1 | 13.4 | 11.7 | 0.8 | 7.9 | 0.8 | 43.5 |
| 20 | 2.3 | 0.2 | 0.2 | 18.2 | 13.9 | 8.2 | 0.9 | 10.3 | 0.8 | 38.2 |
| Average | 2.8 | 0.2 | 1.2 | 15.4 | 13.8 | 9.8 | 0.9 | 9.8 | 0.7 | 39.7 |
| Minimum | 2.3 | 0.1 | 0.2 | 11.1 | 11.2 | 6.5 | 0.6 | 6.2 | 0.3 | 34.5 |
| Maximum | 3.4 | 0.2 | 1.8 | 21.1 | 17.5 | 11.7 | 1.3 | 12.5 | 0.9 | 46.9 |
| Range | 1.1 | 0.1 | 1.6 | 9.9 | 6.3 | 5.3 | 0.7 | 6.4 | 0.6 | 12.4 |

[1] Values expressed as percent of total oil

Plant breeders using the half-seed technique have found it unreliable in selecting stable genetically controlled fatty acid mutations (Stefanson, B. R., In; High and Low Erucic Acid Rapeseed Oils, Ed. N. T. Kenthies, Academic Press, Inc., Canada (1983) pp. 145–159). Although valuable in selecting individuals from a population. the selected traits are not always transmitted to subsequent generations (Rakow, G., and McGregor, D. I., J. Amer. Oil Chem. Soc. (1973) 50:400403. To determine the genetic stability of the selected plants several self-pollinated generations are required (Robelen, G. In; Biotechnology for the Oils and Fats Industry, Ed. C. Ratledge, P. Dawson and J. Rattray, American Oil Chemists Society (1984) pp. 97–105) with chemical analysis of a bulk seed sample.

Mutation breeding has traditionally produced plants carrying, in addition to the trait of interest, multiple, deleterious traits, e.g., reduced plant vigor and reduced fertility. Such traits may indirectly affect fatty acid composition, producing an unstable mutation; and/or reduce yield, thereby reducing the commercial utility of the invention. To eliminate the occurrence of deleterious mutations and reduce the load of mutations carried by the plant a low mutagen dose was used in the seed treatments to create an LD30 population. This allowed for the rapid selection of single gene mutations for fatty acid traits in agronomic backgrounds which produce acceptable yields.

Other than changes in the fatty acid composition of the seed oil, the mutant lines described here have normal plant phenotype when grown under field conditions, and are commercially useful. "Commercial utility" is defined as having a yield, as measured by total pounds of seed or oil produced per acre, within 15% of the average yield of the starting ($M_0$) canola variety grown in the same region. To be commercially useful, plant vigor and high fertility are such that the crop can be produced in this yield by farmers using conventional farming equipment, and the oil with altered fatty acid composition can be extracted using conventional crushing and extraction equipment.

The seeds of several different fatty acid lines have been deposited with the American Type Culture Collection (ATCC, 10801 University Boulevard, Manassas, Va., 20110-2209, U.S.A. and have the following accession numbers.

| Line | Accession # | Deposit Date |
|---|---|---|
| A129.5 | 40811 | May 25, 1990 |
| A133.1 | 40812 | May 25, 1990 |
| M3007.4 | 75022 | June 7, 1991 |
| M3052.6 | 75024 | June 7, 1991 |
| M3062.8 | 75025 | June 7, 1991 |

While the invention is susceptible to various modifications and alternative forms, certain specific embodiments thereof are described in the general methods and examples set forth below. For example the invention may be applied to all Brassica species, including *B. rapa, B. juncea,* and *B. hirta,* to produce substantially similar results. It should be understood, however, that these examples are not intended to limit the invention to the particular forms disclosed but, instead the invention is to cover all modifications, equivalents and alternatives falling within the scope of the invention. This includes the use of somaclonal variation; physical or chemical mutagenesis of plant parts; anther, microspore or ovary culture followed by chromosome doubling; or self- or cross-pollination to transmit the fatty acid trait, alone or in combination with other traits, to develop new Brassica lines.

EXAMPLE 1

Selection of Low FDA Saturates

Prior to mutagenesis, 30,000 seeds of *B. napus* cv. Westar seeds were preimbibed in 300-seed lots for two hours on wet filter paper to soften the seed coat. The preimbibed seeds were placed in 80 mM ethylmethanesulfoante (EMS) for four hours. Following mutagenesis, the seeds were rinsed three times in distilled water. The seeds were sown in 48-well flats containing Pro-Mix. Sixty-eight percent of the mutagenized seed germinated. The plants were maintained at 25° C./15° C., 14/10 hr day/night conditions in the greenhouse. At flowering, each plant was individually self-pollinated.

$M_2$ seed from individual plants were individually catalogued and stored, approximately 15,000 $M_2$ lines was planted in a summer nursery in Carman, Manitoba. The seed from each selfed plant were planted in 3-meter rows with 6-inch row spacing. Westar was planted as the check variety. Selected lines in the field were selfed by bagging the main raceme of each plant. At maturity, the selfed plants were individually harvested and seeds were catalogued and stored to ensure that the source of the seed was known.

Self-pollinated $M_3$ seed and Westar controls were analyzed in 10-seed bulk samples for fatty acid composition via gas chromatography. Statistical thresholds for each fatty acid component were established using a Z-distribution with a stringency level of 1 in 10,000. The selected $M_3$ seeds were planted in the greenhouse along with Westar controls. The seed was sown in 4-inch pots containing Pro-Mix soil and the plants were maintained at 25° C./15° C., 14/10 hr day/night cycle in the greenhouse. At flowering, the terminal raceme was self-pollinated by bagging. At maturity, selfed $M_4$ seed was individually harvested from each plant, labelled, and stored to ensure that the source of the seed was known.

The $M_4$ seed was analyzed in 10-seed bulk samples. Statistical thresholds for each fatty acid component were established from 259 control samples using a Z-distribution of 1 in 800. Selected $M_4$ lines were planted in a field trial in Carman, Manitoba in 3-meter rows with 6-inch spacing. Ten $M_4$ plants in each row were bagged for self-pollination. At maturity, the selfed plants were individually harvested and the open pollinated plants in the row were bulk harvested. The $M_5$ seed from single plant selections was analyzed in 10-seed bulk samples and the bulk row harvest in 50-seed bulk samples.

Selected $M_5$ lines were planted in the greenhouse along with Westar controls. The seed was grown as previously described. At flowering the terminal raceme was self-pollinated by bagging. At maturity, selfed $M_6$ seed was individually harvested from each plant and analyzed in 10-seed bulk samples for fatty acid composition.

Selected $M_6$ lines were entered into field trials in Eastern Idaho. The four trial locations were selected for the wide variability in growing conditions. The locations included Burley, Tetonia, Lamont and Shelley (Table I). The lines were planted in four 3-meter rows with an 8-inch spacing, each plot was replicated four times. The planting design was determined using a Randomized Complete Block Design. The commercial cultivar Westar was used as a check cultivar. At maturity the plots were harvested to determine yield. Yield of the entries in the trial was determined by taking the statistical average of the four replications. The Least Significant Difference Test was used to rank the entries in the randomized complete block design.

TABLE I

Trial Locations for Selected Fatty Acid Mutants

| LOCATION | SITE CHARACTERISTICS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

To determine the fatty acid profile of entries, plants in each plot were bagged for self-pollination. The $M_7$ seed from single plants was analyzed for fatty acids in ten-seed bulk samples.

To determine the genetic relationships of the selected fatty acid mutants crosses were made. Flowers of $M_6$ or later generation mutations were used in crossing. $F_1$ seed was harvested and analyzed for fatty acid composition to determine the mode of gene action. The $F_1$ progeny were planted in the greenhouse. The resulting plants were self-pollinated, the $F_2$ seed harvested and analyzed for fatty acid composition for allelism studies. The $F_2$ seed and parent line seed was planted in the greenhouse, individual plants were self-pollinated. The $F_3$ seed of individual plants was tested for fatty acid composition using 10-seed bulk samples as described previously.

In the analysis of some genetic relationships dihaploid populations were made from the microspores of the $F_1$ hybrids. Self-pollinated seed from diphaloid plants were analyzed for fatty acid analysis using methods described previously.

For chemical analysis, 10-seed bulk samples were hand ground with a glass rod in a 15-mL polypropylene tube and extracted in 1.2 mL 0.25N KOH in 1:1 ether/methanol. The sample was vortexed for 30 sec and heated for 60 sec in a 60° C. water bath. Four mL of saturated NaCl and 2.4 mL of iso-octane were added, and the mixture was vortexed again. After phase separation, 600 $\mu$L of the upper organic phase were pipetted into individual vials and stored under nitrogen at −5° C. One $\mu$L samples were injected into a Supelco SP-2330 fused silica capillary column (0.25 mm ID, 30M length, 0.20 $\mu$m df).

The gas chromatograph was set at 180° C. for 5.5 minutes, then programmed for a 2° C./minute increase to 212° C., and held at this temperature for 1.5 minutes. Total run time was 23 minutes. Chromatography settings were: Column head pressure—15 psi, Column flow (He)—0.7 mL/min,. Auxiliary and Column flow—33 mL/min, Hydrogen flow—33 mL/min, Air flow—400 mL/min, Injector temperature—250° C., Detector temperature—300° C., Split vent—1/15.

Table II describes the upper and lower statistical thresholds for each fatty acid of interest.

TABLE II

Statistical Thresholds for Specific Fatty Acids Derived From Control Westar Plantings

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| $M_3$ Generation (1 in 10,000 rejection rate) | | | | | | |
| Lower | 3.3 | 1.4 | — | 13.2 | 5.3 | 6.0 |
| Upper | 4.3 | 2.5 | 71.0 | 21.6 | 9.9 | 8.3 |

TABLE II-continued

Statistical Thresholds for Specific Fatty Acids
Derived From Control Westar Plantings Percent Fatty Acids

| Genotype | $C_{16:0}$ | $C_{18:0}$ | $C_{18:1}$ | $C_{18:2}$ | $C_{18:3}$ | Sats* |
|---|---|---|---|---|---|---|
| $M_4$ Generation (1 in 800 rejection rate) | | | | | | |
| Lower | 3.6 | 0.8 | — | 12.2 | 3.2 | 5.3 |
| Upper | 6.3 | 3.1 | 76.0 | 32.4 | 9.9 | 11.2 |
| $M_5$ Generation (1 in 755 rejection rate) | | | | | | |
| Lower | 2.7 | 0.9 | — | 9.6 | 2.6 | 4.5 |
| Upper | 5.7 | 2.7 | 80.3 | 26.7 | 9.6 | 10.0 |

*Sats = Total Saturate Content

At the $M_3$ generation, twelve lines exceeded the lower statistical threshold for palmitic acid ($\leq 3.3\%$). Line W13097.4 had 3.1% palmitic acid and an FDA saturate content of 4.5%. After a cycle in the greenhouse, $M_4$ seed from line W13097.4 (designated line A144) was analyzed. Line W13097.4.1 (A144.1) had 3.1% $C_{16:0}$, exceeding the lower statistical threshold of 3.6%. The FDA saturate content for A144.1 was 4.5%. The fatty acid compositions for the $M_3$, $M_4$ and $M_5$ generations of this family are summarized in Table III.

TABLE III

Fatty Acid Composition of a Low Palmitic Acid/Low FDA
Saturate Canola Line Produced by Seed Mutagenesis Percent Fatty Acids

| Genotype[a] | $C_{16:0}$ | $C_{18:0}$ | $C_{18:1}$ | $C_{18:2}$ | $C_{18:3}$ | Sats[b] | Tot Sat[c] |
|---|---|---|---|---|---|---|---|
| Westar | 3.9 | 1.9 | 67.5 | 17.6 | 7.4 | 5.9 | 7.0 |
| W13097.4 ($M_3$) | 3.1 | 1.4 | 63.9 | 18.6 | 9.5 | 4.5 | 5.6 |
| W13097.4 ($M_4$) | 3.1 | 1.4 | 66.2 | 19.9 | 6.0 | 4.5 | 5.5 |
| A144.1.9 ($M_5$) | 2.9 | 1.4 | 64.3 | 20.7 | 7.3 | 4.4 | 5.3 |

[a]Letter and numbers up to second decimal point indicate the plant line. Number after second decimal point indicates an individual plant.
[b]Sat = FDA Saturates
[c]Tot Sat = Total Saturate Content The $M_5$ seed of ten self-pollinated A144.1 (ATCC 40813) plants averaged 3.1% palmitic acid and 4.7% FDA saturates. One selfed plant (A144.1.9) contained 2.9% palmitic acid and FDA saturates of 4.4%. Bulk seed analysis from open-pollinated (A144.1) plants at the $M_5$ generation averaged 3.1% palmitic acid and 4.7% FDA saturates. The fatty acid composition of the bulked and individual A144.1 lines are summarized in Table IV.

TABLE IV

Fatty Acid Composition of A144
Low Palmitic Acid/Low FDA Saturate Line

Percent Fatty Acids

| Genotype[a] | $C_{16:0}$ | $C_{18:0}$ | $C_{18:1}$ | $C_{18:2}$ | $C_{18:3}$ | Sats[b] | Tot Sat[c] |
|---|---|---|---|---|---|---|---|
| Individually Self-Pollinated Plants | | | | | | | |
| A144.1.1 | 3.2 | 1.6 | 64.4 | 20.5 | 7.0 | 4.8 | 5.9 |
| A144.1.2 | 3.0 | 1.5 | 67.4 | 18.6 | 6.3 | 4.5 | 5.7 |
| A144.1.3 | 3.6 | 1.8 | 61.4 | 22.4 | 7.5 | 5.2 | 6.6 |
| A144.1.4 | 3.2 | 1.5 | 64.6 | 20.9 | 6.7 | 4.7 | 5.8 |
| A144.1.5 | 3.3 | 1.7 | 60.0 | 23.9 | 7.9 | 5.0 | 6.1 |
| A144.1.6 | 3.1 | 1.4 | 67.3 | 17.8 | 6.5 | 4.6 | 5.2 |
| A144.1.7 | 3.1 | 1.6 | 67.7 | 17.4 | 6.5 | 4.8 | 5.4 |
| A144.1.8 | 3.1 | 1.8 | 66.9 | 18.7 | 6.1 | 4.9 | 5.4 |
| A144.1.9 | 2.9 | 1.4 | 64.3 | 20.7 | 7.3 | 4.4 | 5.3 |
| A144.1.10 | 3.1 | 1.5 | 62.5 | 20.4 | 7.7 | 4.6 | 5.6 |
| Average of Individually Self-Pollinated Plants | | | | | | | |
| A144.1.1-10 | 3.1 | 1.6 | 64.8 | 20.1 | 6.9 | 4.7 | 5.7 |
| Bulk Analysis of Open-Pollinated Plants | | | | | | | |
| A144.1B | 3.1 | 1.6 | 64.8 | 19.4 | 7.8 | 4.7 | 5.7 |

[a]Letter and numbers up to second decimal point indicate the plant line. Number after second decimal point indicates an individual plant.
[b]Sat = FDA Saturates
[c]Tot Sat = Total Saturate Content These reduced levels have remained stable to the $M_7$ generations in both greenhouse and field conditions. These reduced levels have remained stable to the $M_7$ generation in multiple location field trails. Over all locations, the self-pollinated plants (A144) averaged 2.9% palmitic acid and FDA saturates of 4.6%. The fatty acid composition of the A144 lines for each Idaho location are summarized in Table V. In the multiple location replicated trial the yield of A144 was not significantly different in yield from the parent cultivar Westar. By means of seed mutagenesis, the level of saturated fatty acids of canola (*B. napus*) was reduced from 5.9% to 4.6%. The palmitic acid content was reduced from 3.9% to 2.9%.

TABLE V

Fatty Acid Composition of a Mutant
Low Palmitic Acid/Low FDA Saturate
Canola Line at Different Field Locations in Idaho

| Trial Location | Percent Fatty Acids | | | | | | |
|---|---|---|---|---|---|---|---|
| | $C_{16:0}$ | $C_{18:0}$ | $C_{18:1}$ | $C_{18:2}$ | $C_{18:3}$ | Sats | Tot Sats |
| Burley | 2.9 | 1.3 | 62.3 | 20.6 | 10.3 | 4.2 | 5.0 |
| Tetonia | 2.9 | 1.7 | 59.7 | 21.0 | 11.2 | 4.6 | 5.7 |
| Lamont | 3.1 | 1.8 | 63.2 | 19.5 | 9.0 | 4.9 | 5.9 |
| Shelley | 2.8 | 1.9 | 64.5 | 18.8 | 8.8 | 4.7 | 5.9 |

To determine the genetic relationship of the palmitic acid mutation in A144 ($C_{16:0}$—3.0%, $C_{18:0}$—1.5%, $C_{18:1}$—67.4%, $C_{18:2}$—18.6%, $C_{18:3}$—6.3%) to other fatty acid mutations it was crossed to A129 a mutant high oleic acid acid ($C_{16:0}$—3.8%, $C_{18:0}$—2.3%, $C_{18:1}$—75.6), $C_{18:2}$—9.5%, $C_{18:3}$—4.9%). Over 570 dihaploid progeny produced from the $F_1$ hybrid were harvested and analyzed for fatty acid composition. The results of the progeny analysis are summarized in Table VB. Independent segregation of the palmitic traits was observed which demonstrates that the genetic control of palmitic acid in A144 is different from the high oleic acid mutation in A129.

TABLE VB

Genetic Studies of Dihaploid Progeny of A144 × A129

| Genotype | $C_{16:0}$ Content (%) | Frequency Observed | Expected |
|---|---|---|---|
| p−p−p2−p2− | 3.0% | 162 | 143 |
| p+p+p2−p2− | 3.4% | 236 | 286 |
| p+p+p2+p2+ | 3.8% | 175 | 143 |

EXAMPLE 2

An additional low FDA saturate line, designated A149.3 (ATCC 40814), was also produced by the method of Example 1. A 50-seed bulk analysis of this line showed the following fatty acid composition: $C_{16:0}$—3.6%, $C_{18:0}$—1.4%, $C_{18:1}$—65.5%, $C_{18:2}$—18.3%, $C_{18:3}$—8.2%, FDA Sats—5.0%, Total Sats—5.9%. This line has also stably maintained its mutant fatty acid composition to the $M_5$ generation. In a multiple location replicated trial the yield of A149 was not significantly different in yield from the parent cultivar Westar.

EXAMPLE 3

An additional low palmitic acid and low FDA saturate line, designated M3094.4 (ATCC 75023), was also produced by the method of Example 1. A 10-seed bulk analysis of this line showed the following fatty acid composition: $C_{16:0}$—2.7%, $C_{18:0}$—1.6%, $C_{18:1}$—66.6%, $C_{18:2}$—20.0%, $C_{18:3}$—6.1%, $C_{20:1}$—1.4%, $C_{22:1}$—0.0%, FDA Saturate—4.3%, Total Saturates—5.2%. This line has stably maintained its mutant fatty acid composition to the $M_5$ generation. In a single replicated trial the yield of M3094 was not significantly different in yield from the parent cultivar.

M3094.4 was crossed to A144, a low palmitic acid mutation (Example 1) for allelism studies. Fatty acid composition of the $F_2$ seed showed the two lines to be allelic. The mutational events in A144 and M3094, although different in origin, are in the same gene.

EXAMPLE 4

In the studies of Example 1, at the $M_3$ generation, 470 lines exceed the upper statistical threshold for palmitic acid L≧4.3%). One $M_3$ line, W14538.6, contained 9.2% palmitic acid. Selfed progenies of this line, since designated M3007.4 (ATCC 75022), continued to exceed to the upper statistical threshold for high palmitic acid at both the $M_4$ and $M_5$ generations with palmitic acid levels of 11.7% and 9.1%, respectively. The fatty acid composition of this high palmitic acid mutant, which was stable to the $M_7$ generation under both field and greenhouse conditions, is summarized in Table VI.

TABLE VI

Fatty Acid Composition of a High Palmitic Acid Canola Line Produced by Seed Mutagenesis

| | Percent Fatty Acids | | | | | |
|---|---|---|---|---|---|---|
| Genotype[a] | $C_{16:0}$ | $C_{18:0}$ | $C_{18:1}$ | $C_{18:2}$ | $C_{18:3}$ | Sats* |
| Westar | 3.9 | 1.9 | 67.5 | 17.6 | 7.4 | 7.0 |
| W14538.6 ($M_3$) | 8.6 | 1.6 | 56.4 | 20.3 | 9.5 | 10.2 |
| M3007.2 ($M_4$) | 11.7 | 2.1 | 57.2 | 18.2 | 5.1 | 13.9 |
| M3007.4 ($M_5$) | 9.1 | 1.4 | 63.3 | 13.7 | 5.5 | 12.7 |

*Sats = Total Saturate Content

To determine the genetic relationship of the high palmitic mutation in M3007.4 to the low palmitic mutation in A144 (Example 1) crosses were made. The $F_2$ progeny were analyzed for fatty acid composition. The data presented in Table VIB shows the high palmitic group ($C_{16:0}$>7.0%) makes up one-quarter of the total population analyzed. The high palmitic acid mutation was controlled by one single gene mutation.

TABLE VIB

Genetic Studies of M3007 × A144

| Genotype | $C_{16:0}$ Content (%) | Frequency Observed | Expected |
|---|---|---|---|
| p−p−/p−hp− | <7.0 | 151 | 142 |
| hp−hp− | >7.0 | 39 | 47 |

An additional $M_3$ line, W4773.7, contained 4.5% palmitic acid. Selfed progenies of this line, since designated A200.7 (ATCC 40816), continued to exceed the upper statistical threshold for high palmitic acid in both the $M_4$ and $M_5$ generations with palmitic acid levels of 6.3% and 6.0%, respectively. The fatty acid composition of this high palmitic acid mutant, which was stable to the $M_7$ generation under both field and greenhouse conditions, is summarized in Table VII.

TABLE VII

Fatty Acid Composition of a High Palmitic Acid Canola Line Produced by Seed Mutagenesis

| | Percent Fatty Acids | | | | | |
|---|---|---|---|---|---|---|
| Genotype[a] | $C_{16:0}$ | $C_{18:0}$ | $C_{18:1}$ | $C_{18:2}$ | $C_{18:3}$ | Sats* |
| Westar | 3.9 | 1.9 | 67.5 | 17.6 | 7.4 | 7.0 |
| W4773.7 ($M_3$) | 4.5 | 2.9 | 63.5 | 19.9 | 7.1 | 9.3 |
| W4773.7.7 ($M_4$) | 6.3 | 2.6 | 59.3 | 20.5 | 5.6 | 10.8 |
| A200.7.7 ($M_5$) | 6.0 | 1.9 | 60.2 | 20.4 | 7.3 | 9.4 |

*Sats = Total Saturate Content

EXAMPLE 5

Selection of Low Stearic Acid Canola Lines

In the studies of Example 1, at the $M_3$ generation, 42 lines exceeded the lower statistical threshold for stearic acid (<1.4%). Line W14859.6 had 1.3% stearic acid. At the $M_5$ generation, its selfed progeny (M3052.1) continued to fall within the lower statistical threshold for $C_{18:0}$ with 0.8% stearic acid. The fatty acid composition of this low stearic acid mutant, which was stable under both field and greenhouse conditions is summarized in Table VIII. In a single location replicated yield trial M3052.1 was not significantly different in yield from the parent cultivar Westar.

TABLE VIII

Fatty Acid Composition of a Low
Stearic Acid Canola Line Produced by Seed Mutagenesis

| Genotype[a] | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 5.9 |
| W14859.6 ($M_3$) | 5.3 | 1.3 | 56.1 | 23.7 | 9.6 | 7.5 |
| M3052.1 ($M_4$) | 4.9 | 0.9 | 58.9 | 22.7 | 9.3 | 5.8 |
| M3052.6 ($M_5$) | 4.4 | 0.8 | 62.1 | 21.2 | 7.9 | 5.2 |

To determine the genetic relationship of the low stearic acid mutation of M3052.1 to other fatty acid mutations it was crossed to the low palmitic acid mutation A144 (Example 1). Seed from over 300 dihaploid progeny were harvested and analyzed for fatty acid composition. The results are summarized in Table VIB. Independent segregation of the palmitic acid and stearic acid traits was observed. The low stearic acid mutation was genetically different from the low palmitic acid mutations found in A144 and M3094.

TABLE VIIIB

Genetic Studies of M3052 × A144

| Genotype | $C_{16:0}$ + $C_{18:0}$ Content (%) | Frequency | |
|---|---|---|---|
| | | Observed | Expected |
| p-p-s-s- | <4.9% | 87 | 77 |
| p-p-s-s-/p+p+s-s- | 4.0% < X < 5.6% | 152 | 154 |
| p+p+s+s+ | >5.6% | 70 | 77 |

An additional $M_5$ line, M3051.10, contained 0.9% and 1.1% stearic acid in the greenhouse and field respectively. A ten-seed analysis of thie line showed the following fatty acid composition: $C_{16:0}$—3.9%, $C_{18:0}$—1.1%, $C_{18:1}$—61.7%, $C_{18:2}$—23.0%, $C_{18:3}$—7.6%, FDA saturates—5.0%, Total Saturates—5.8%. In a single location replicated yield trial M3051.10 was not significantly different in yield from the parent cultivar Westar. M3051.10 was crossed to M3052.1 for allelism studies. Fatty acid composition of the $F_2$ seed showed the two lines to be allelic. The mutational events in M3051.10 and M3052.1 although different in origin were in the same gene.

An additional M5 line, M3054.7, contained 1.0% and 1.3% stearic acid in the greenhouse and field respectively. A ten-seed analysis of this line showed the following fatty acid composition: $C_{16:0}$—4.0%, $C_{18:0}$—1.0%, $C_{18:1}$—66.5%, $C_{18:2}$—18.4%, $C_{18:3}$—7.2%, FDA saturates—5.0%, Total Saturates—6.1%. In a single location replicated yield trial M3054.7 was not significantly different in yield from the parent cultivar Westar. M3054.7 was crossed to M3052.1 for allelism studies. Fatty acid composition of the $F_2$ seed showed the two lines to be allelic. The mutational events in M3054.7, M3051.10 and M3052.1 although different in origin were in the same gene.

EXAMPLE 6

High Oleic Acid Canola Lines

In the studies of Example 1, at the $M_3$ generation, 31 lines exceeded the upper statistical threshold for oleic acid L≧71.0%). Line W7608.3 had 71.2% oleic acid. At the $M_4$ generation, its selfed progeny (W7608.3.5, since designated A129.5) continued to exceed the upper statistical threshold for $C_{18:1}$ with 78.8% oleic acid. $M_5$ seed of five self-pollinated plants of line A129.5 (ATCC 40811) averaged 75.0% oleic acid. A single plant selection, A129.5.3 had 75.6% oleic acid. The fatty acid composition of this high oleic acid mutant, which was stable under both field and greenhouse conditions to the $M_7$ generation, is summarized in Table IX. This line also stably maintained its mutant fatty acid composition to the $M_7$ generation in field trials in multiple locations. Over all locations the self-pollinated plants (A129) averaged 78.3% oleic acid. The fatty acid composition of the A129 for each Idaho trial location are summarized in Table X. In multiple location replicated yield trials, A129 was not significantly different in yield from the parent cultivar Westar.

The canola oil of A129, after commercial processing, was found to have superior oxidative stability compared to Westar when measured by the Accelerated Oxygen Method (AOM), American Oil Chemists' Society Official Method Cd 12-57 for fat stability; Active Oxygen Method (revised 1989). The AOM of Westar was 18 AOM hours and for A129 was 30 AOM hours.

TABLE IX

Fatty Acid Composition of a High
Oleic Acid Canola Line Produced by Seed Mutagenesis

| Genotype[a] | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W7608:3 ($M_3$) | 3.9 | 2.4 | 71.2 | 12.7 | 6.1 | 7.6 |
| W7608.3.5 ($M_4$) | 3.9 | 2.0 | 78.8 | 7.7 | 3.9 | 7.3 |
| A129.5.3 ($M_5$) | 3.8 | 2.3 | 75.6 | 9.5 | 4.9 | 7.6 |

Sats = Total Saturate Content

TABLE X

Fatty Acid Composition of a Mutant High
Oleic Acid Line at Different Field Locations in Idaho

| Location | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Burley | 3.3 | 2.1 | 77.5 | 8.1 | 6.0 | 6.5 |
| Tetonia | 3.5 | 3.4 | 77.8 | 6.5 | 4.7 | 8.5 |
| Lamont | 3.4 | 1.9 | 77.8 | 7.4 | 6.5 | 6.3 |
| Shelley | 3.3 | 2.6 | 80.0 | 5.7 | 4.5 | 7.7 |

Sats = Total Saturate Content

The genetic relationship of the high oleic acid mutation A129 to other oleic desaturases was demonstrated in crosses made to commercial canola cultivars and a low linolenic acid mutation. A129 was crossed to the commercial cultivar Global ($C_{16:0}$—4.5%, $C_{18:0}$—1.5%, $C_{18:1}$—62.9%, $C_{18:2}$—20.0%, $C_{18:3}$—7.3%). Approximately 200 $F_2$ individuals were analyzed for fatty acid composition. The results are summarized in Table XB. The segregation fit 1:2:1 ratio suggesting a single co-dominant gene controlled the inheritance of the high oleic acid phenotype.

TABLE XB

Genetic Studies of A129 × Global

| Genotype | $C_{18:1}$ Content (%) | Frequency Observed | Frequency Expected |
|---|---|---|---|
| od−od− | 77.3 | 43 | 47 |
| od−od+ | 71.7 | 106 | 94 |
| od+od+ | 66.1 | 49 | 47 |

A cross between A129 and IMC 01, a low linolenic acid variety ($C_{16:0}$—4.1%, $C_{18:0}$—1.9%, $C_{18:1}$—66.4%, $C_{18:2}$—18.1%, $C_{18:3}$—5.7%), was made to determine the inheritance of the oleic acid desaturase and linoleic acid desaturase. In the $F_1$ hybrids both the oleic acid and linoleic acid desaturase genes approached the mid-parent values indicating a co-dominant gene actions. Fatty acid analysis of the $F_2$ individuals confirmed a 1:2:1:2:4:2:1:2:1 segregation of two independent, co-dominant genes (Table XC).

TABLE XC

Genetic Studies of A129 × IMC 01

| Genotype | Ratio | Frequency Observed | Frequency Expected |
|---|---|---|---|
| od−od−ld−ld− | 1 | 11 | 12 |
| od−od−ld−ld+ | 2 | 30 | 24 |
| od−od−ld+ld+ | 1 | 10 | 12 |
| od−od+ld−ld− | 2 | 25 | 24 |
| od−od+ld−ld+ | 4 | 54 | 47 |
| od−od+ld+ld+ | 2 | 18 | 24 |
| od+od+ld−ld− | 1 | 7 | 12 |
| od+od+ld−ld+ | 2 | 25 | 24 |
| od+od+ld+ld+ | 1 | 8 | 12 |

An additional high oleic acid line, designated A128.3, was also produced by the disclosed method. A 50-seed bulk analysis of this line showed the following fatty acid composition: $C_{16:0}$—3.5%, $C_{18:0}$—1.8%, $C_{18:1}$—77.3%, $C_{18:2}$—9.0%, $C_{18:3}$—5.6%, FDA Sats—5.3%, Total Sats—6.4%. This line also stably maintained its mutant fatty acid composition to the $M_7$ generation. In multiple locations replicated yield trials, A128 was not significantly different in yield from the parent cultivar Westar.

A129 was crossed to A128.3 for allelism studies. Fatty acid composition of the $F_2$ seed showed the two lines to be allelic. The mutational events in A129 and A128.3 although different in origin were in the same gene.

An additional high oleic acid line, designated M3028.-10 (ATCC75026), was also produced by the disclosed method in Example 1. A 10-seed bulk analysis of this line showed the following fatty acid composition: $C_{16:0}$—3.5%, $C_{18:0}$—1.8%, $C_{18:1}$—77.3%, $C_{18:2}$—9.0%, $C_{18:3}$—5.6%, FDA Saturates—5.3%, Total Saturates—6.4%. In a single location replicated yield trial M3028.10 was not significantly different in yield from the parent cultivar Westar.

EXAMPLE 7

Low Linoleic Acid Canola

In the studies of Example 1, at the $M_3$ generation, 80 lines exceeded the lower statistical threshold for linoleic acid ($\leq 13.2\%$). Line W12638.8 had 9.4% linoleic acid. At the $M_4$ and $M_5$ generations, its selfed progenies [W12638.8, since designated A133.1 (ATCC 40812)] continued to exceed the statistical threshold for low $C_{18:2}$ with linoleic acid levels of 10.2% and 8.4%, respectively. The fatty acid composition of this low linoleic acid mutant, which was stable to the $M_7$ generation under both field and greenhouse conditions, is summarized in Table XI. In multiple location replicated yield trials, A133 was not significantly different in yield from the parent cultivar Westar. An additional low linoleic acid line, designated M3062.8 (ATCC 75025), was also produced by the disclosed method. A 10-seed bulk analysis of this line showed the following fatty acid composition: $C_{16:0}$—3.8%, $C_{18:0}$—2.3%, $C_{18:1}$—77.1%, $C_{18:2}$—8.9%, $C_{18:3}$—4.3%, FDA Sats—6.1%. This line has also stably maintained its mutant fatty acid composition in the field and greenhouse.

TABLE XI

Fatty Acid Composition of a Low Linoleic Acid Canola Line Produced by Seed Mutagenesis

| Genotype[a] | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats[b] |
| Westar | 3.9 | 1.9 | 67.5 | 17.6 | 7.4 | 7.0 |
| W12638.8 ($M_3$) | 3.9 | 2.3 | 75.0 | 9.4 | 6.1 | 7.5 |
| W12638.8.1 ($M_4$) | 4.1 | 1.7 | 74.6 | 10.2 | 5.9 | 7.1 |
| A133.1.8 ($M_5$) | 3.8 | 2.0 | 77.7 | 8.4 | 5.0 | 7.0 |

[a]Letter and numbers up to second decimal point indicate the plant line. Number after second decimal point indicates an individual plant.
[b]Sats = Total Saturate Content

EXAMPLE 8

Low Linolenic and Linoleic Acid Canola

In the studies of Example 1, at the $M_3$ generation, 57 lines exceeded the lower statistical threshold for linolenic acid ($\leq 5.3\%$). Line W14749.8 had 5.3% linolenic acid and 15.0% linoleic acid. At the $M_4$ and $M_5$ generations, its selfed progenies [W14749.8, since designated M3032 (ATCC 75021)] continued to exceed the statistical threshold for low $C_{18:3}$ with linolenic acid levels of 2.7% and 2.3%, respectively, and for a low sum of linolenic and linoleic acids with totals of 11.8% and 12.5% respectively. The fatty acid composition of this low linolenic acid plus linoleic acid mutant, which was stable to the $M_5$ generation under both field and greenhouse conditions, is summarized in Table XII. In a single location replicated yield trial M3032 was not significantly different in yield from the parent cultivar (Westar).

TABLE XII

Fatty Acid Composition of a Low Linolenic Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W14749.8 ($M_3$) | 4.0 | 2.5 | 69.4 | 15.0 | 5.3 | 6.5 |
| M3032.8 ($M_4$) | 3.9 | 2.4 | 77.9 | 9.1 | 2.7 | 6.4 |
| M3032.1 ($M_5$) | 3.5 | 2.8 | 80.0 | 10.2 | 2.3 | 6.5 |

Sats = Total Saturate Content

19

EXAMPLE 9

The high oleic acid mutation of A129 was introduced into different genetic backgrounds by crossing and selecting for fatty acids and agronomic characteristics. A129 (now renamed IMC 129) was crossed to Legend, a commercial spring *Brassica napus* variety. Legend has the following fatty acid composition: $C_{16:0}$—3.8%, $C_{18:0}$—2.1%, $C_{18:1}$—63.1%, $C_{18:2}$—17.8%, $C_{18:3}$—9.3%. The cross and progeny resulting from were coded as 89B60303.

The $F_1$ seed resulting from the cross was planted in the greenhouse and self-pollinated to produce $F_2$ seed. The $F_2$ seed was planted in the field for evaluation. Individual plants were selected in the field for agronomic characteristics. At maturity, the $F_3$ seed was harvested from each selected plant and analyzed for fatty acid composition.

Individuals which had fatty acid profiles similar to the high oleic acid parent (IMC 129) were advanced back to the field. Seeds ($F_3$) of selected individuals were planted in the field as selfing rows and in plots for preliminary yield and agronomic evaluations. At flowering the $F_3$ plants in the selfing rows were self-pollinated. At maturity the $F_4$ seed was harvested from individual plants to determine fatty acid composition. Yield of the individual selections was determined from the harvested plots.

Based on fatty acid composition of the individual plants and yield and agronomic characteristics of the plots $F_4$ lines were selected and advanced to the next generation in the greenhouse. Five plants from each selected line were self-pollinated. At maturity the $F_5$ seed was harvested from each and analyzed for fatty acid composition.

The $F_5$ line with the highest oleic acid fatty profile was advanced to the field as a selfing row. The remaining $F_5$ seed from the five plants was bulked together for planting the yield plots in the field. At flowering, the $F_5$ plants in each selfing-row were self-pollinated. At maturity the $F_6$ self-pollinated seed was harvest from the selfing row to determine fatty acid composition and select for the high oleic acid trait. Yield of the individual selections was determined from the harvested plots.

Fifteen $F_6$ lines having the high oleic fatty profile of IMC 129 and the desired agronomic characteristics were advanced to the greenhouse to increase seed for field trialing. At flowering the $F_6$ plants were self-pollinated. At maturity the $F_7$ seed was harvested and analyzed for fatty acid composition. Three $F_7$ seed lines which had fatty acid profiles most similar to IMC 129 (Table XIII) were selected and planted in the field as selfing rows, the remaining seed was bulked together for yield trialing. The high oleic fatty acid profile of IMC 129 was maintained through seven generations of selection for fatty acid and agronomic traits in an agronomic background of *Brassica napus* which was different from the parental lines. Thus, the genetic trait from IMC 129 for high oleic acid can be used in the development of new high oleic Brassica napus varieties.

TABLE XIII

Fatty Acid Composition of Advanced Breeding Generation with High Oleic Acid Trait (IMC 129 X Legend)

| $F_7$ Selections of 89B60303 | Fatty Acid Composition (%) | | | | |
|---|---|---|---|---|---|
| | $C_{16:0}$ | $C_{18:0}$ | $C_{18:1}$ | $C_{18:2}$ | $C_{18:3}$ |
| 93.06194 | 3.8 | 1.6 | 78.3 | 7.7 | 4.4 |
| 93.06196 | 4.0 | 2.8 | 77.3 | 6.8 | 3.4 |
| 93.06198 | 3.7 | 2.2 | 78.0 | 7.4 | 4.2 |

The high oleic acid trait of IMC 129 was also introduced into a different genetic background by combining crossing and selection methods with the generation of dihaploid populations from the microspores of the $F_1$ hybrids. IMC 129 was crossed to Hyola 41, a commercial spring *Brassica napus* variety. Hyola 41 has the following fatty acid composition: $C_{16:0}$—3.8%, $C_{18:0}$—2.7%, $C_{18:1}$—64.9%, $C_{18:2}$—16.2%, $C_{18:3}$—9.1%. The cross and progeny resulting from the cross were labeled 90DU.146.

The $F_1$ seed was planted from the cross and a dihaploid ($DH_1$) population was made from the $F_1$ microspores using standard procedures for *Brassica napus*. Each $DH_1$ plant was self-pollinated at flowering to produce $DH_1$ seed. At maturity the $DH_1$ seed was harvested and analyzed for fatty acid composition. $DH_1$ individuals which expressed the high oleic fatty acid profit of IMC 129 were advanced to the next generation in the greenhouse. For each individual selected five $DH_1$ seeds were planted. At flowering the $DH_2$ plants were self-pollinated. At maturity the $DH_2$ seed was harvested and analyzed for fatty acid composition. The $DH_2$ seed which was similar in fatty acid composition to the IMC 129 parent was advanced to the field as a selfing row. The remaining $DH_2$ seed of that group was bulked and planted in plots to determine yield and agronomic characteristics of the line. At flowering individual $DH_3$ plants in the selfing row were self-pollinated. At maturity the $DH_3$ seed was harvested from the individual plants to determine fatty acid composition. Yield of the selections was determined from the harvested plots. Based on fatty acid composition, yield and agronomic characteristics selections were advanced to the next generation in the greenhouse. The $DH_4$ seed produced in the greenhouse by self-pollination was analyzed for fatty acid composition. Individuals which were similar to the fatty acid composition of the IMC 129 parent were advanced to the field to test for fatty acid stability and yield evaluation. The harvested $DH_5$ seed from six locations maintained the fatty acid profile of the IMC 129 parent (Table XIV).

TABLE XIV

Fatty Acid Composition of Advanced Dihaploid Breeding Generation with High Oleic Acid Trait (IMC 129 X Hyola 41)

| DH5 of 90DU.146 at Multiple Locations | Fatty Acid Composition (%) | | | | |
|---|---|---|---|---|---|
| | $C_{16:0}$ | $C_{18:0}$ | $C_{18:1}$ | $C_{18:2}$ | $C_{18:3}$ |
| Aberdeen | 3.7 | 2.6 | 75.4 | 8.1 | 7.2 |
| Blackfoot | 3.3 | 2.4 | 75.5 | 8.8 | 7.5 |
| Idaho Falls | 3.7 | 3.1 | 75.0 | 7.5 | 8.1 |
| Rexberg | 3.9 | 3.7 | 75.3 | 7.0 | 6.5 |
| Swan Valley | 3.5 | 3.4. | 74.5 | 7.0 | 7.3 |
| Lamont | 3.9 | 2.8 | 72.0 | 10.1 | 8.4 |

What is claimed is:

1. An edible canola oil obtained from a bulk sample of seeds from a single Brassica line, said oil having an oleic acid content of from about 71.0 percent to about 78.8 percent, a linoleic acid content of from about 7.7 percent to about 12.7 percent, a α-linolenic acid content of from about 3.9 percent to about 6.1 percent and an erucic acid content of less than about 2 percent, said contents determined after hydrolysis and extraction, wherein said line is designated A129.5, A133.1 or M3062.8 and has American Type Culture Collection accession number 40811, 40812 or 75025. respectively.

2. The edible oil of claim 1, wherein said oil has an FDA saturated fatty acid content of from about 6.3 to about 7.7.

3. The oil of claim 1, said oil having an oleic acid content of from about 74.6 percent to about 77.7 percent, a linoleic acid content of from about 8.4 percent to about 10.2 percent, an α-linolenic acid content of from about 5.0 percent to about 6.1 percent and an erucic acid content of less than about 2 percent, said contents determined after hydrolysis and extraction.

4. The oil of claim 1, wherein said line is designated A129.5 and has American Type Culture Collection number 40811.

5. An edible canola oil obtained from a bulk sample of seeds from a single Brassica line, said oil having a palmitic acid content from about 7.0 percent to about 11.7 percent, a linoleic acid content of from about 13.7 percent to about 20.3 percent, and an erucic acid content of less than about 2 percent, said contents determined after hydrolysis and extraction, wherein said line is designated M3007.4 and has American Type Culture Collection accession number 75022.

6. The edible oil of claim 5, wherein said palmitic fatty acid content is greater than about 9.1 percent.

7. The edible oil of claim 5, wherein said oil has an FDA saturates content of from about 10.2 percent to about 13.9 percent, a palmitic acid content of from 8.6 percent to about 11.7 percent, an oleic acid content of from about 56.4 percent to about 63.3 percent and α-linolenic acid content of from about 5.1 percent to about 9.5 percent.

8. An edible canola oil obtained from a bulk sample of seeds from a single Brassica line, said oil having a palmitic acid content from about 6.0 percent to about 11.7 percent, a linoleic acid content of from about 13.7 percent to about 20.5 percent, an α-linolenic acid content of from about 5.1 percent to about 7.3 percent, and an erucic acid content of less than about 2 percent, said contents determined after hydrolysis and extraction, wherein said line is designated M3007.4 and has American Type Culture Collection accession number 75022.

9. The edible oil of claim 8, wherein said oil has an FDA saturates content of from about 9.4 percent to about 13.9 percent and an oleic acid content of from about 57.2 percent to 63.3 percent.

10. An edible canola oil derived from a bulk sample of seeds from a single Brassica line, said oil having a stearic acid content of from about 0.8 percent to about 1.1 percent, a linoleic acid content from about 18.4 percent to about 23.0 percent, an α-linolenic acid content of from about 7.2 percent to about 9.3 percent, and an erucic acid content of less than about 2 percent, said contents determined after hydrolysis and extraction, wherein said line is designated M3052.6 and has American Type Culture Collection Number 75024.

11. The edible oil of claim 10, wherein said oil has a α-linolenic acid content of from about 7.2 percent to about 7.9 percent.

12. A method of producing an edible canola oil comprising the steps of:

a) crushing a bulk quantity of seeds from a single Brassica line; and b) obtaining said oil from said crushed seeds, said oil having an oleic acid content of from about 71.0 percent to about 78.8 percent, a linoleic acid content of from about 7.7 percent to about 12.7 percent, a α-linolenic acid content of from about 3.9 percent to about 6.1 percent and an erucic acid content of less than about 2 percent, said contents determined after hydrolysis and extraction, wherein said line is designated A129.5, A133.1 or M3062.8 and has American Type Culture Collection accession number 40811, 40812 or 75025, respectively.

13. A method of producing an edible canola oil comprising the steps of:

a) crushing a bulk quantity of seeds from a single Brassica line; and b) obtaining said oil from said crushed seeds, said oil having a palmitic acid content from about 7.0 percent to about 11.7 percent, a linoleic acid content of from about 13.7 percent to about 20.3 percent, and an erucic acid content of less than about 2 percent, said contents determined after hydrolysis and extraction, wherein said line is designated M3007.4 and has American Type Culture Collection accession number 75022.

14. A method of producing an edible canola oil comprising the steps of:

a) crushing a bulk quantity of seeds from a single Brassica line; and b) obtaining said oil from said crushed seeds, said oil having a stearic acid content from about 0.8 percent to about 1.1 percent, a linolenic acid content from about 18.4 percent to about 23.0 percent, an α-linolenic acid content from about 7.2 percent to about 9.3 percent, and an erucic acid content of less than about 2 percent, said contents determined after hydrolysis and extraction, wherein said line is designated M3052.6 and has American Type Culture Collection accession number 75024.

15. A canola oil extracted from Brassica seeds designated A129.5, A133.1 or M3062.8 and having American Type Culture Collection accession number 40811, 40812 or 75025, respectively.

16. A canola oil extracted from Brassica seeds designated M3007.4 and having American Type Culture Collection accession number 75022.

17. A canola oil extracted from Brassica seeds designated M3052.6 and having American Type Culture Collection accession number 75024.

* * * * *